United States Patent [19]
Pierce et al.

[11] Patent Number: 6,090,119
[45] Date of Patent: Jul. 18, 2000

[54] CORNEAL INCISION DEVICE

[75] Inventors: Robert W. Pierce, Wrentham; Joseph F. Keenan, Cohasset; Dana Michael Cote, Lynn; Edwin G. Lee, Burlington, all of Mass.

[73] Assignee: Becton Dickinson and Company, Franklin Lakes, N.J.

[21] Appl. No.: 09/163,964

[22] Filed: Sep. 30, 1998

[51] Int. Cl.$^7$ .................................................. A61F 9/00
[52] U.S. Cl. ..................... 606/166; 606/107; 606/167; 606/185; 604/22
[58] Field of Search ............... 604/19, 22; 606/107, 606/159, 166, 167, 170, 171, 185, 184

[56] References Cited

U.S. PATENT DOCUMENTS

| 4,796,623 | 1/1989 | Krasner et al. | |
|---|---|---|---|
| 4,844,060 | 7/1989 | Krumeich. | |
| 5,290,301 | 3/1994 | Lieberman | 606/166 |
| 5,486,188 | 1/1996 | Smith | 606/166 |
| 5,571,124 | 11/1996 | Zelman | 606/166 |
| 5,586,980 | 12/1996 | Kremer et al. | 606/166 |
| 5,611,805 | 3/1997 | Hall | 606/166 |
| 5,779,723 | 7/1998 | Schwind | 606/166 |
| 5,876,415 | 3/1999 | Pierce et al. | 606/166 |

*Primary Examiner*—Glenn K. Dawson
*Attorney, Agent, or Firm*—Arthur D. Dawson; Keith J. McWha

[57] ABSTRACT

A corneal incision device includes a surgical blade and a frame having an inner surface with a configuration that is generally in the shape of a ring-like segment of a hollow sphere. The frame has an aperture therein to allow the surgical blade to be inserted through the frame beyond the inner surface. The aperture is sized and shaped to allow movement of the surgical blade in one axis. The device may have a protuberance affixed to the inner surface of the frame adjacent to the aperture disposed to distort a surface of a patient's eye when the device is selectively positioned on the eye by a practitioner. The device has provisions for holding, advancing and withdrawing the surgical blade through the aperture, disposed on the frame. The device is releasably retained on the patient's eye by fixation elements disposed on the inner surface of the frame. There is a handle affixed to the frame to facilitate the practitioner's manipulation of device.

15 Claims, 12 Drawing Sheets

CORNEAL INCISION DEVICE

FIELD OF INVENTION

The present invention relates to surgical scalpels and more particularly to a device for making a precise incision in the eye of a patient.

BACKGROUND

Generally in surgical procedures, a practitioner makes an incision in the body of a patient in order to repair damaged tissue, modify tissue, remove tissue or to insert some sort of implantable device. Many procedures are combinations of these procedures. One example of such a combination is found in cataract surgery. Cataract surgery is performed to remove the lens of a patient's eye that has become substantially or partially opaque having an adverse effect on the patient's visual acuity. Practitioners have found that if the opacified lens is removed and replaced with an implantable intraocular lens (IOL), there are significant improvements in the patient's visual acuity. In order to perform this procedure, the practitioner makes an incision in the patient's eye sufficient to remove the non-functional lens and insert an appropriate IOL. The incision to facilitate the removal and replacement of the lens is made in the cornea or sclera of the eye. The incision provides the practitioner with access to the lens so that it may be removed.

There are a number of different procedures that are used to remove a non-functional lens from the eye, the most commonly practiced are referred to as extracapsular surgery and phacoemulsification. In extracapsular surgery, the practitioner removes the lens while allowing the posterior lens capsule to remain. In phacoemulsification, the practitioner reduces the lens to an emulsion by careful application of ultrasonic energy coupled with irrigation and suction, thereby removing the non-functional lens. In both of these procedures, the removed lens is then replaced by a synthetic polymeric IOL substantially restoring the visual acuity of the eye.

A critical component of this procedure is the incision that provides the practitioner with access to the non-functional natural lens so that it can be removed. The ideal incision for a lens removal and replacement is of a minimum size and accurately placed. The incision through which the several instruments used to conduct the procedure is preferably an opening substantially the same circumference as the instruments. Accurate sizing minimizes trauma to the eye and facilitates healing of the eye after the procedure is completed. In the case of the phacoemulsion procedure, if the incision is too small, corneal tissue adjacent the incision may be damaged by contact with the ultrasonic probe and alternatively, if the incision is too large, leakage from the eye may cause prolapse and loss of endothelial cells.

Another problem related to the incision in cataract surgery is suture induced astigmatism. An incision made in the eye must be closed after the procedure so that healing occurs and that there is no path for infection. Previously, sutures have been used to close the incision. A suture may alter the shape of the eye and result in astigmatism. Additionally, sutures may cause irritation, provide a location for infection and abscess or a foreign body reaction. Recently, sutureless techniques have been devised that allow the practitioner to make an incision of a particular shape or geometry that utilize the internal pressure in the eye to keep the incision closed until it heals without the use of sutures. Making such an accurately placed and sized incision for such a procedure is very technique sensitive. Apparatus and methods for making a properly sized and shaped incision for cataract removal procedures are available, but are still subject to variations in technique. If a device that made a practitioner's placement and sizing of an incision in the eye less technique sensitive, the art of eye surgery would be advanced. Such a device and a method for its use is disclosed hereinbelow.

SUMMARY

A corneal incision device of the present invention includes a surgical blade and a frame having an inner surface with a configuration that is generally in the shape of a ring-like segment of a hollow sphere. The frame has an aperture therein to allow the surgical blade to be inserted through the frame beyond the inner surface. The aperture defines a longitudinal axis and is sized and shaped to allow movement of the surgical blade in the longitudinal axis. The device has provisions for holding, advancing and withdrawing the surgical blade through the aperture, disposed on the frame. The device is releasably retained on the patient's eye by fixation elements disposed on the inner surface of the frame. There is a grip affixed to the frame to facilitate the practitioner's manipulation of device.

The device of the invention allows the practitioner to achieve a correct placement and precise shape for the desired incision. Once the practitioner has selectively positioned the device on the patient's eye, the surgical blade is correctly positioned and ready for selective activation by the practitioner. A further benefit of the blade placement provision is that the sharp blade is kept in a protected position until its use is desired by the practitioner. The device of the invention represents an improvement in the practitioner's ability to form, rapidly and correctly, a selectively precisely shaped incision in the patient's eye thereby improving the efficiency of a widely practiced and difficult procedure.

DETAILED DESCRIPTION

Figure 1:
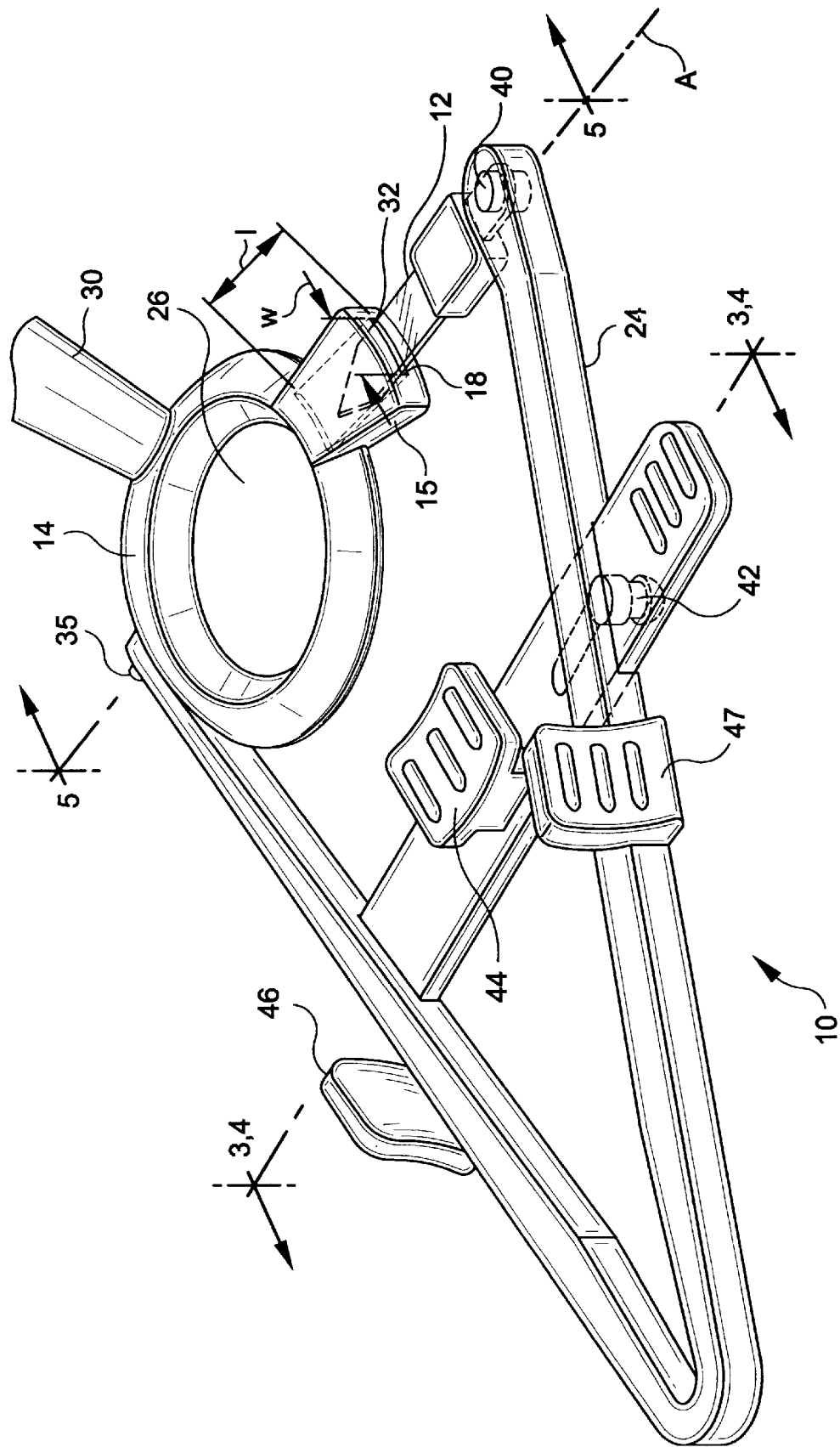
FIG. 1 is a perspective view of a preferred embodiment of the multi-plane corneal incision device of the invention.
Figure 2:
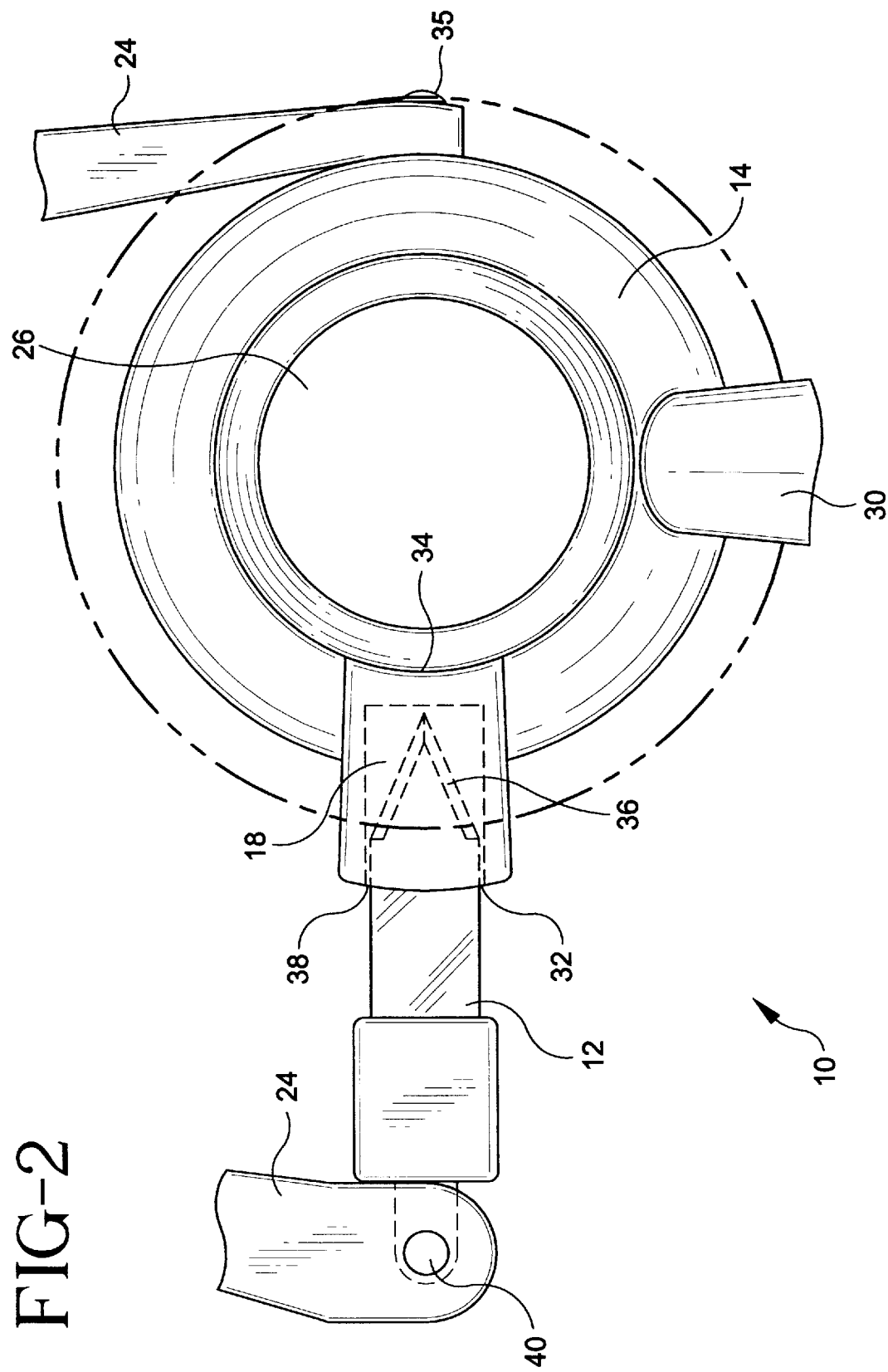
FIG. 2 is a partial top plan view of the device of FIG. 1.
Figure 3:
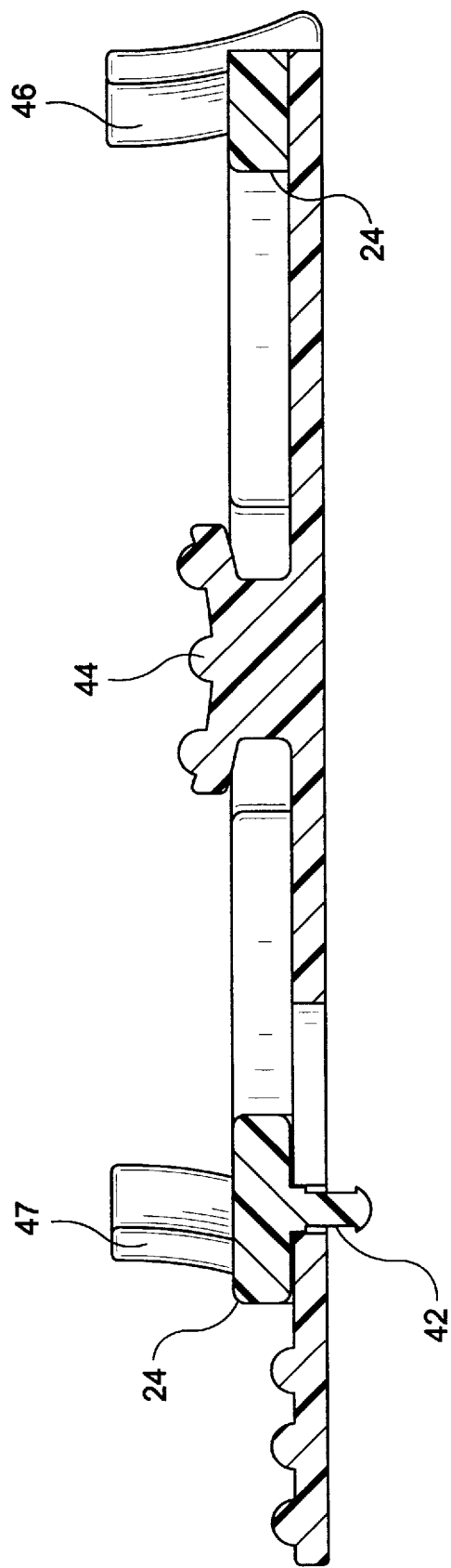
FIG. 3 is a cross-sectional view of the device of FIG. 1, along the line 3—3 with the latch in the first position.
Figure 4:
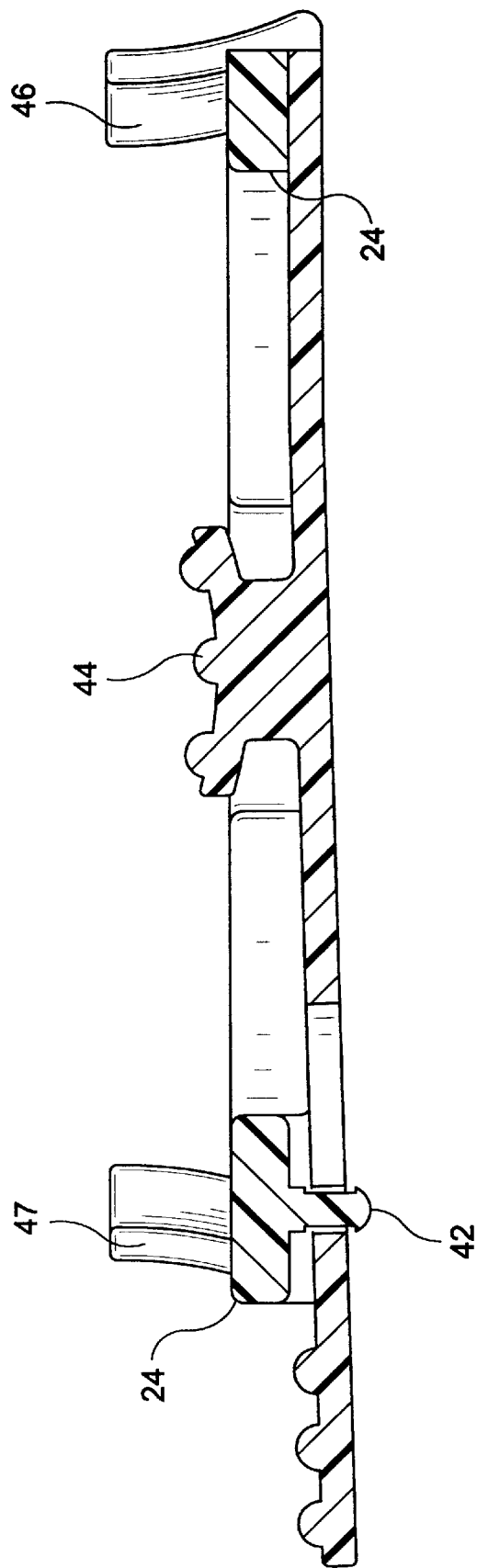
FIG. 4 is a cross-sectional view of the device of FIG. 1, analogous to FIG. 3, with the latch in the second position.

While this invention is satisfied by embodiments in many different forms, there is shown in the drawings and herein described in detail preferred embodiments of the invention with the understanding that the present disclosure is to be considered exemplary of the principles of the invention and is not intended to limit the invention to the embodiments illustrated. The scope of the invention is measured by the appended claims and their equivalents.

Referring to FIGS. 1—7, a corneal incision device 10 of the present invention includes a surgical blade 12, a frame 14 having an inner surface 16 with a configuration that is generally in the shape of a ring-like segment of a hollow sphere. Frame 14 defines an aperture 18 therein, preferably within a projecting portion 15, to allow surgical blade 12 to be inserted through frame 14 beyond inner surface 16. Aperture 18 defines an axis A, is sized and shaped to allow movement of surgical blade 12 in substantially only one axis.

Figure 6:
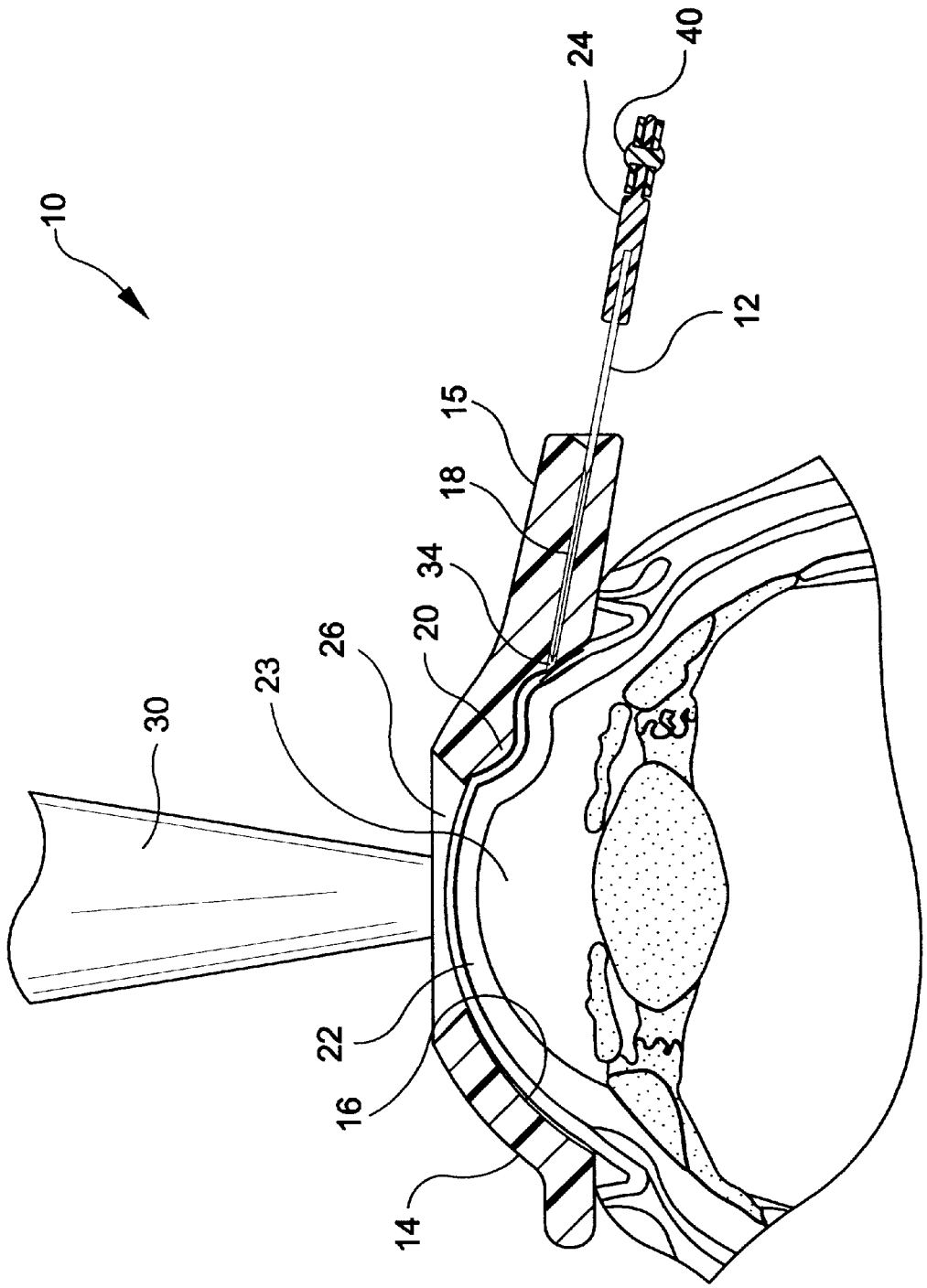
FIG. 6 is a schematic cross-sectional view of an alternate embodiment of the device of FIG. 1 analogous to FIG. 5.
Figure 7:
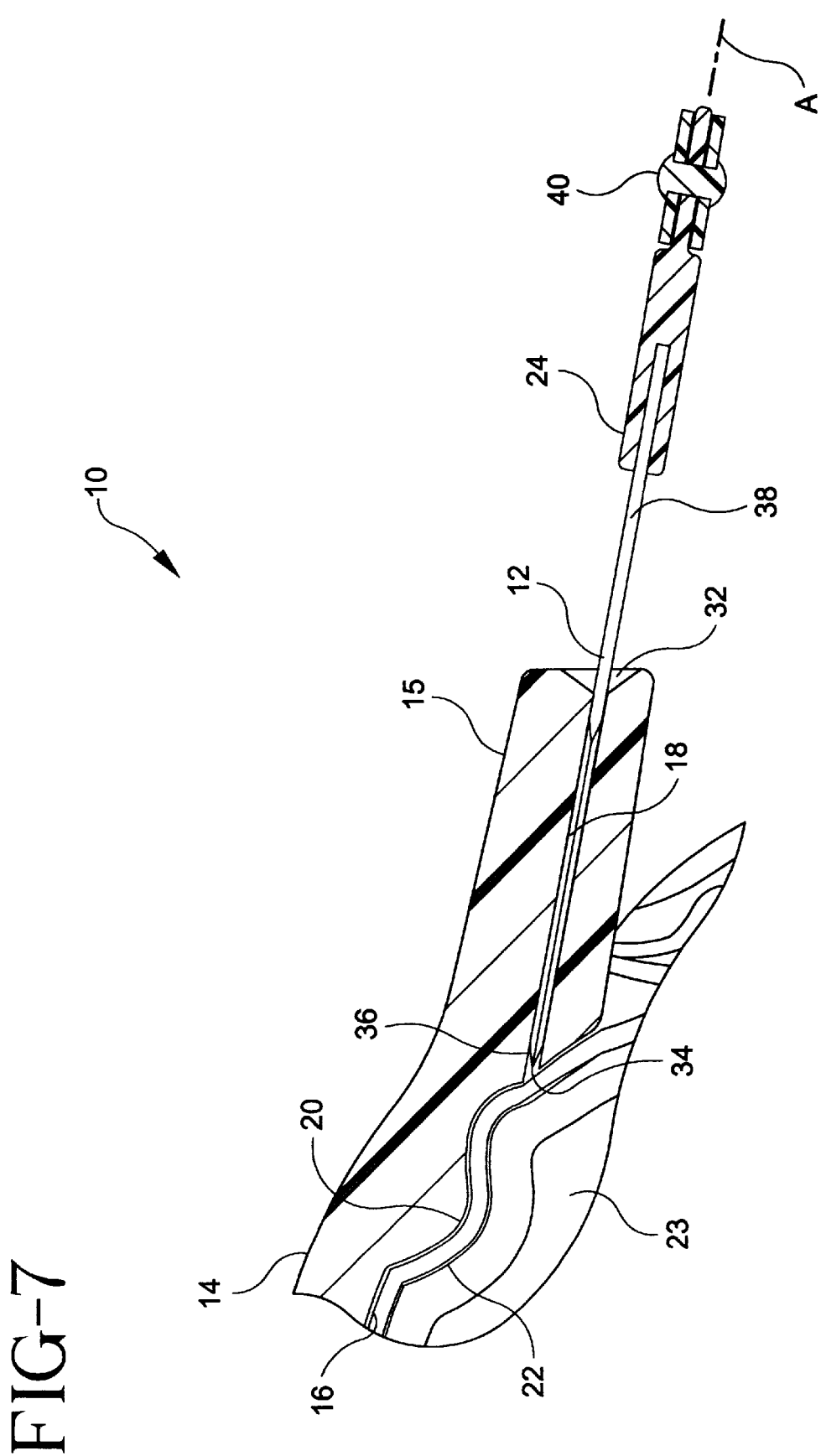
FIG.7 is an enlarged cross-sectional detail of the device of FIG. 1 taken from FIG. 6.

In one embodiment, there is a protuberance 20, best seen in FIG. 6, affixed to inner surface 16 of the frame adjacent to aperture 18. Protuberance 20 is disposed to distort a surface 22 of a patient's eye 23 when device 10 is selectively positioned on eye 23 by a practitioner.

Blade 12 is attached to a cantilever 24 that is disposed on frame 14 to hold, advance and withdraw blade 12 through aperture 18. Preferably, cantilever 24 is either neutral in or biased to a rest position where blade 12 is in the position wherein blade 12 is contained within aperture 18. There is an opening 26 through frame 14 to inner surface 16. Opening 26 is disposed so that when a selectively applied vacuum source device is applied to frame 14 while device 10 is selectively placed on the eye of a patient by the practitioner, ambient air pressure retains device 10 in the selected position as long as the vacuum source is maintained. Other provisions for retention of frame 14 onto the patient's eye such as lateral ridges, a plurality of points, a plurality of bumps on inside surface 16 may be used either in combination with, or instead of, the vacuum source. Additionally, the bumps and ridges may be formed from a resilient material and applied to the inside surface. There is a grip, preferably finger grips as seen in FIGS. 1–6 in combination with or instead of a handle 30 affixed to frame 14 to facilitate the practitioner's manipulation of device 10. Aperture 18 of multi-plane corneal incision device 10 has a proximal opening 32, a longitudinal axis "A" and a distal opening 34 on inside surface 16 of frame 14.

In the embodiment where inside surface 16 includes protuberance 20, distal opening 34 is substantially coterminous with protuberance 20 so that when device 10 is selectively positioned on patient's eye 23 and blade 12 is advanced through distal opening 34, an incision is made through the surface into the anterior chamber of the eye in a region of the eye surface 22 conformed to protuberance 20.

One type of procedure that device 10 is suited for is referred to as a clear cornea procedure. For this procedure, blade 12 preferably is a keratome or slit blade. Blade 12 preferably has a spear shaped beveled sharp tip 36 as a cutting surface and sides 38 that are dull with respect to tip 36. Aperture 18 is sized, shaped and disposed so sharp tip cutting surface 36 can extend into the aperture a sufficient distance to cause the desired incision in the patient's eye when it is selectively advanced by the practitioner. A width "w" of aperture 18 should not be sufficient more than the width of blade 12 and a height "h" of the aperture should not be sufficiently greater than the thickness of blade 12 to allow movement of the blade substantially more than in one axis. The width clearance preferably is less than about 0.05 mm and the height clearance is preferably less than about 0.01.

These clearances only allow the selective movement of the blade substantially in one axis with respect to frame 14. For other types of procedures, other blade shapes may be preferred and are considered within the scope of the disclosure.

The distortion of the patient's eye surface 22 by protuberance 20 when device 10 is selectively positioned on the patient's eye results in the incision made by advancement of blade 12 having a complicated multi-plane geometry. As described above, such an incision generally is able to close and heal without the need for sutures. The exact shape of protuberance 20 and the exact position of aperture 18 in relation to the protuberance is dependent on the desired geometry of the incision to be made. Generally, the desired shape of the incision is substantially "S" shaped. For applications where a planar incision is desired, a tangent line angle α best seen in FIG. 5, where the incision contacts the outer surface of the cornea is about twelve degrees to about twenty degrees and preferably an incidence angle of about seventeen and one half degrees is selected for the axis "A" of the aperture to interior surface 16 of frame 14. For other procedures and types of incisions other incidence angles may be preferred and are considered within the scope of this disclosure.

Figure 5:
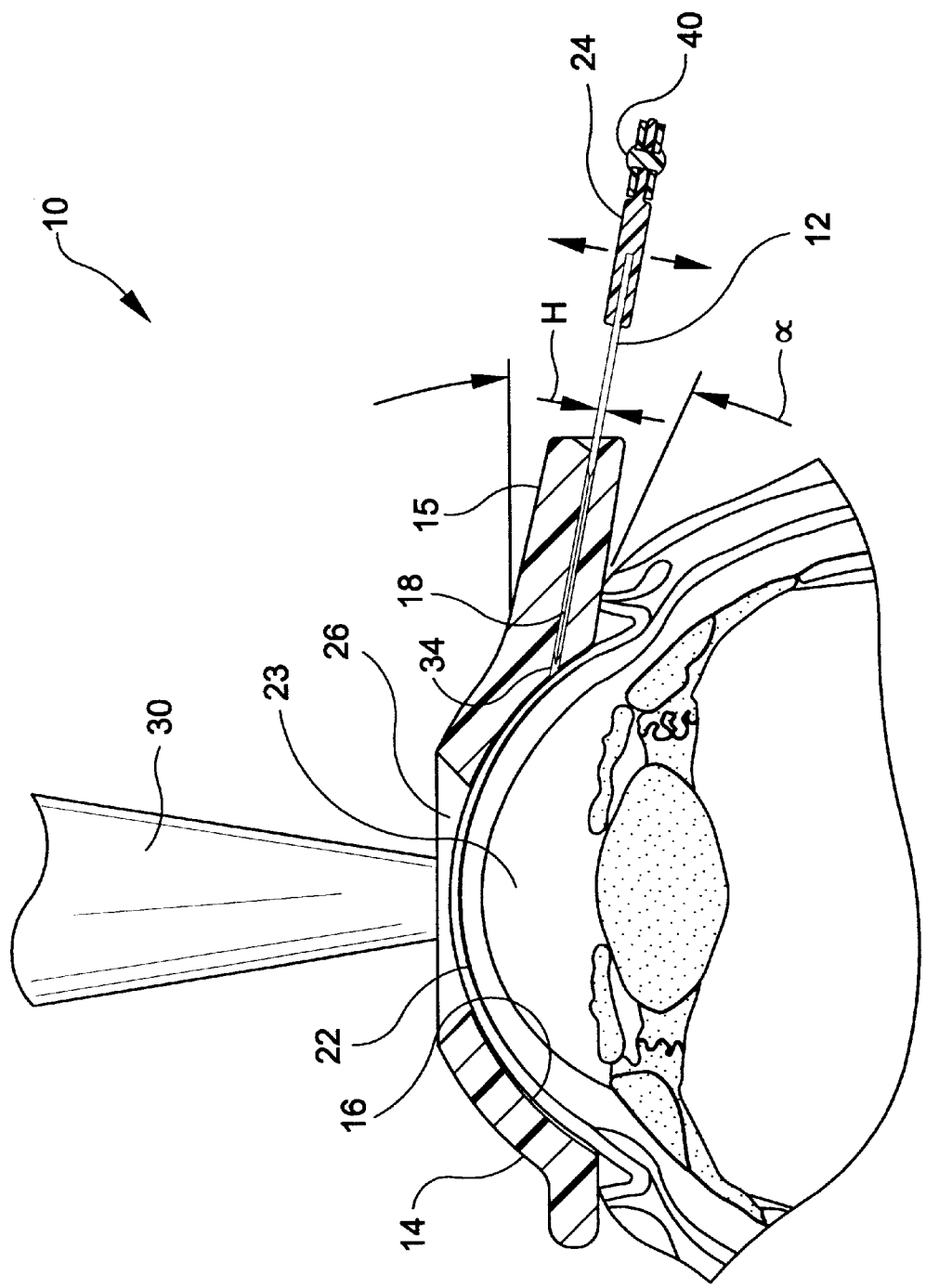
FIG. 5 is a schematic cross-sectional view of the device of FIG. 1 taken along the line 5—5 as mounted on the eye of a patient.

Referring to FIGS. 1–7, cantilever 24 is disposed from a pivot position 35 on a first side of frame 14, preferably about diametrically opposite aperture 18, to attach to blade 12 at a second pivot, preferably a ball and socket 40, disposed to facilitate movement of blade 12 through aperture 18. Other types of pivots may be envisioned, and are considered within the scope of this disclosure. Preferably, cantilever 24 includes a selectively releasable latch 42 with a finger release 44, so that if a practitioner holds device 10 between the thumb and middle finger, using grips 46 and 47, respectively, the practitioner's index finger is positioned on finger release 44. In use, the practitioner would selectively position device 10 on patient's eye as schematically illustrated in FIG. 5, using finger grips 46 and 47 in conjunction with handle 30. When the desired positioning is obtained, the practitioner would use the index finger to apply sufficient pressure on finger release 44 to release latch 42 and apply sufficient squeezing pressure to cantilever 24 to move blade 12 from aperture 18 to project beyond inner surface 16 and form the desired incision through patient's eye surface 22. After forming the incision, the practitioner releases the pressure on grips 46 and 47 thus allowing cantilever 24 to return blade 12 to the rest position within aperture 18.

Suitable materials for forming frame 14 include, but are not limited to metallic materials such as stainless steel, titanium and the like, polymeric materials such as polycarbonate, polysulfone, acrylonitrile/butadiene/styrene (ABS), and the like. Scalpel blade 12 may be formed from stainless steel, polymeric materials such as polycarbonate, acrylics and the like, or ceramics such as zirconia, diamond, silicon and titanates. Cantilever 24 may be integrally formed with frame 24 or formed separately and assembled. When materials are selected for forming components of device 10, compatibility with various sterilization procedures must be considered.

FIGS. 7, 8, 9, 10, 11 and 12 illustrate other embodiments of the multi-plane corneal incision device of the invention. In these embodiments, alternates to cantilever 24 are disposed on frame 14 at projection 15 to hold, advance and withdraw blade 12 through aperture 18. FIGS. 1–12 illustrate advancing and withdrawing means selected from the group consisting of a manually activated cantilever arm, a mechanical release including a bias spring, an electrical solenoid, a hydraulically actuated mechanism, a pneumatically actuated mechanism, a vacuum actuated mechanism, a cam and cam follower, a cable release against a mechanical biasing spring and combinations thereof. Accordingly, substantially similar components that perform substantially similar functions are numbered identically to those components of the embodiments of FIGS. 1–6 except that a hundreds digit is used to identify those components of FIGS. 7–12. Additional equivalent embodiments to hold, advance and withdraw blade 12 through aperture 18 may be envisioned by one skilled in the art after study of this disclosure. These equivalents are considered within the scope of the disclosure.

Figure 8:
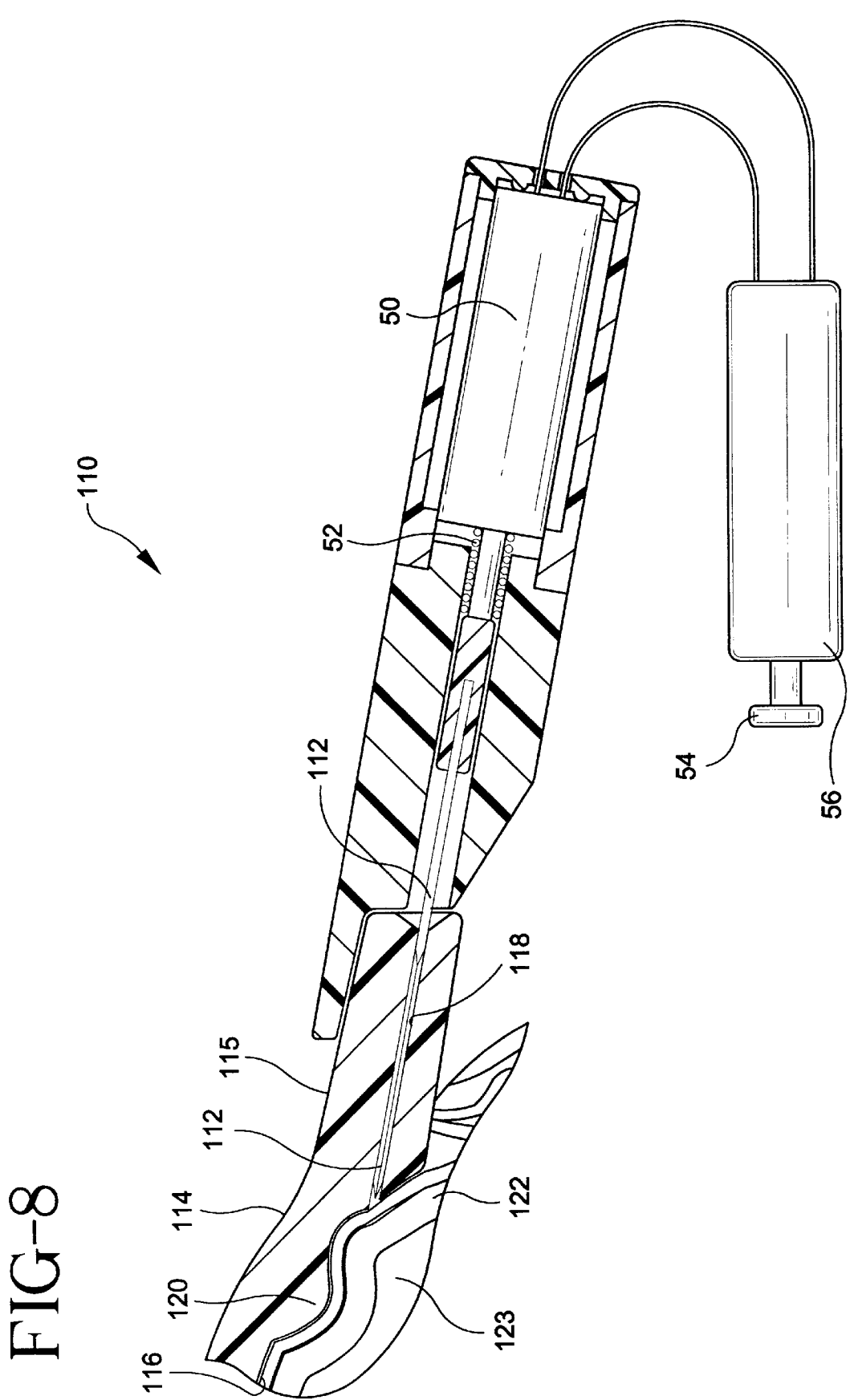
FIG. 8 is an enlarged cross-sectional detail analogous to FIG. 7 with an alternate blade movement system.

Referring to FIG. 8, projecting portion 115 from frame 114 of device 110 is illustrated. In this embodiment, an electrical solenoid 50 with a bias spring 52 is activated by a switch 54 on a power source 56. When solenoid 50 is not activated, bias spring 52 keeps blade 112 within aperture 118. When solenoid 50 is activated by the practitioner, blade 112 is urged to project beyond inner surface 116 of frame 114 and form the desired incision through surface 122 into the anterior chamber of patient eye 123.

Figure 9:
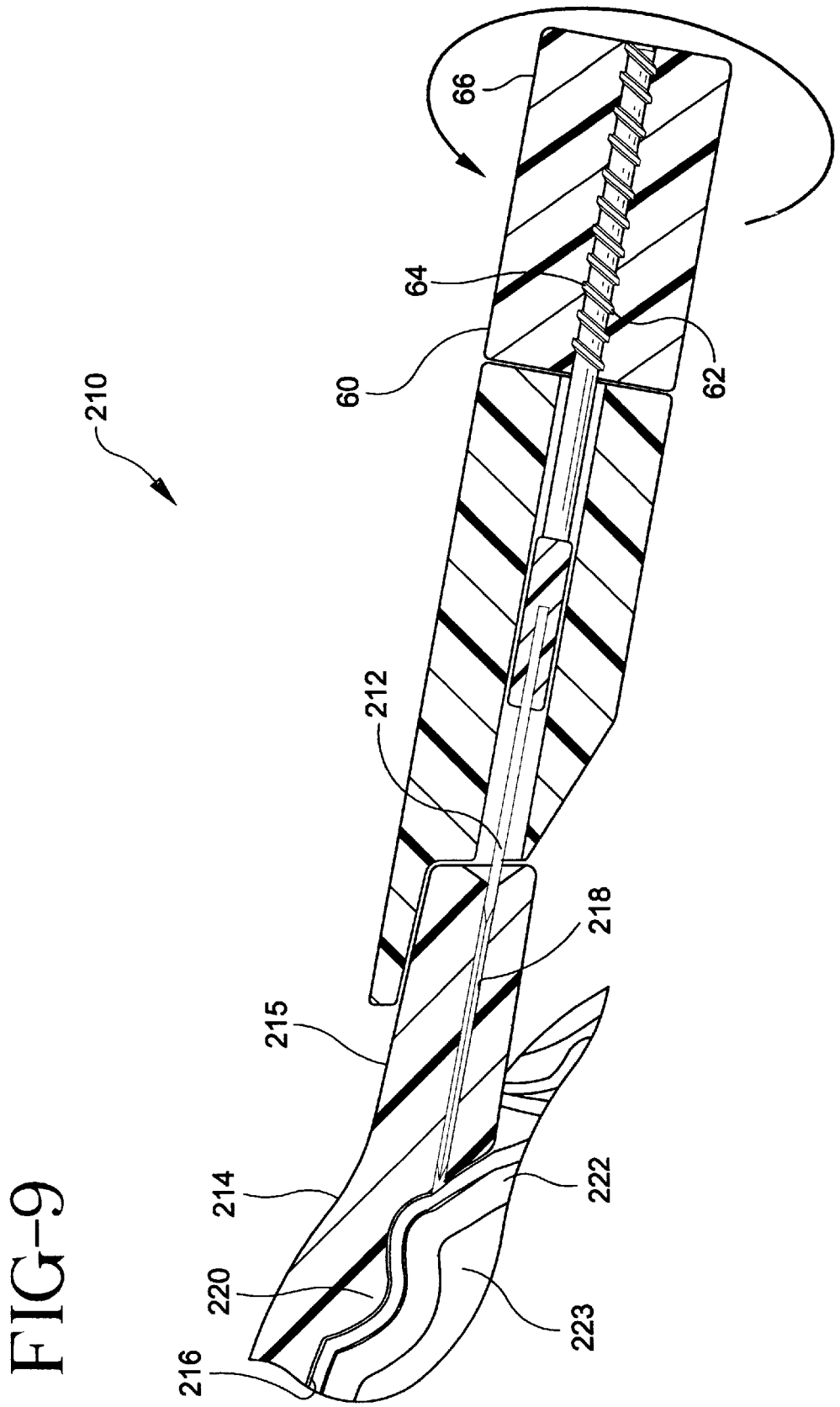
FIG. 9 is analogous to the view of FIG. 7 with another blade movement system.

Referring to FIG. 9, projecting portion 215 from frame 214 of device 210 is illustrated. In this embodiment a mechanical threaded advance and retraction mechanism 60 is mounted on projecting portion 215. The practitioner turns a knob 66 in a first direction so that conjugate threads 62 and 64 selectively advance blade 212 through aperture 218. When blade 212 is advanced beyond inner surface 216 of frame 214 a sufficient distance, desired incision is formed through surface 222 into the anterior chamber of patient eye 223. Blade 212 is selectively withdrawn back into aperture 218 by turning knob in the reverse direction to return blade 212 to the origination position.

Figure 10:
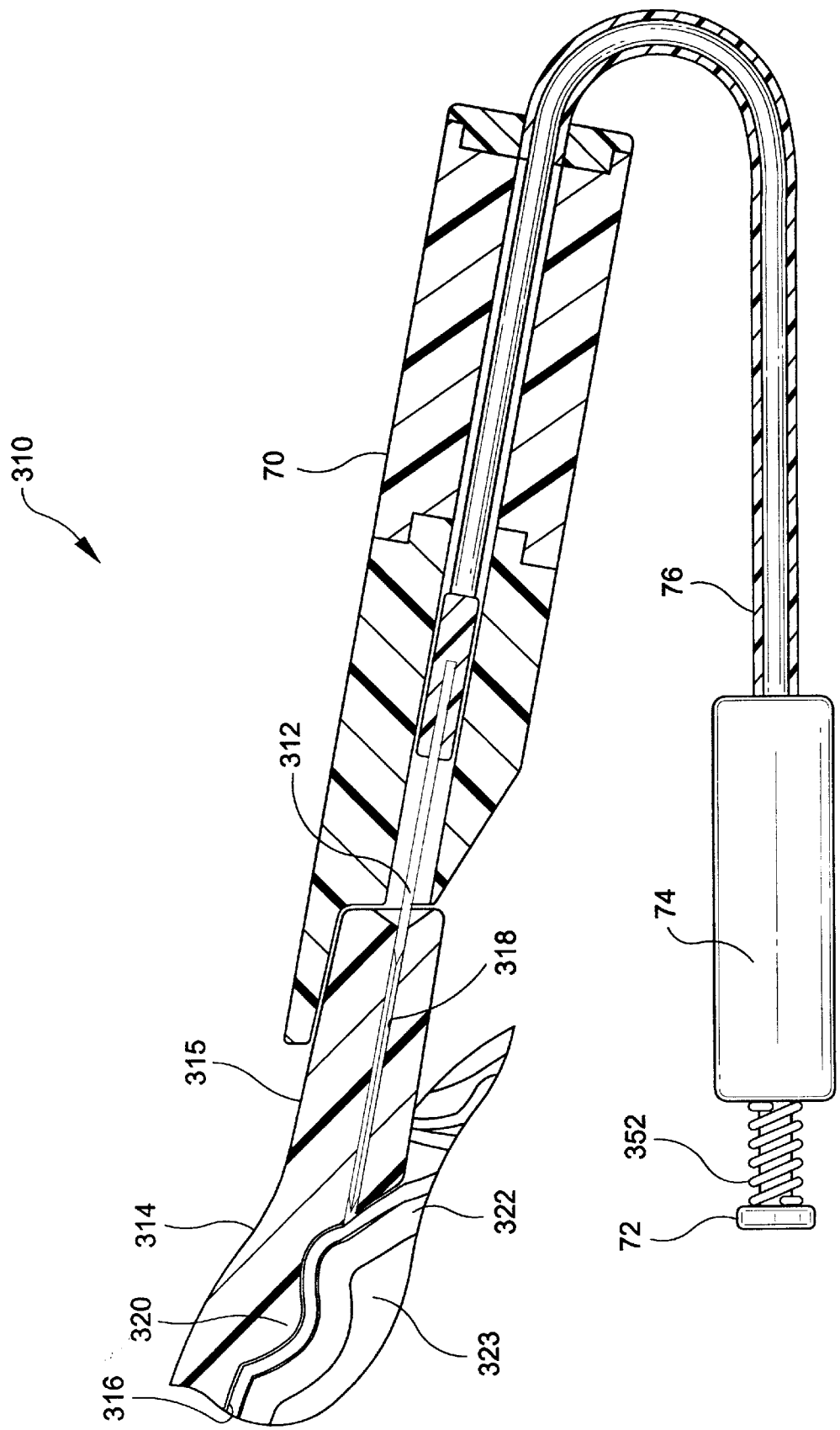
FIG. 10 is analogous to the view of FIG. 7 with yet another blade movement system.

Referring to FIG. 10, projecting portion 315 from frame 314 of device 310 is illustrated. Projecting portion 315 includes a mechanical cable control mechanism 70 with a button release 72 mounted on a finger support 74 that is attached to a cover connecting cable 76. Finger support 74 includes a bias spring 352 that is overcome by the practitioner's finger pressure sufficient to advance blade 312 to project beyond inner surface 316 to form the desired incision through surface 322 into the anterior chamber of patient eye 323. When the practitioner releases the pressure from button release 72, spring 352 returns blade 312 to the original position within aperture 318.

Figure 11:
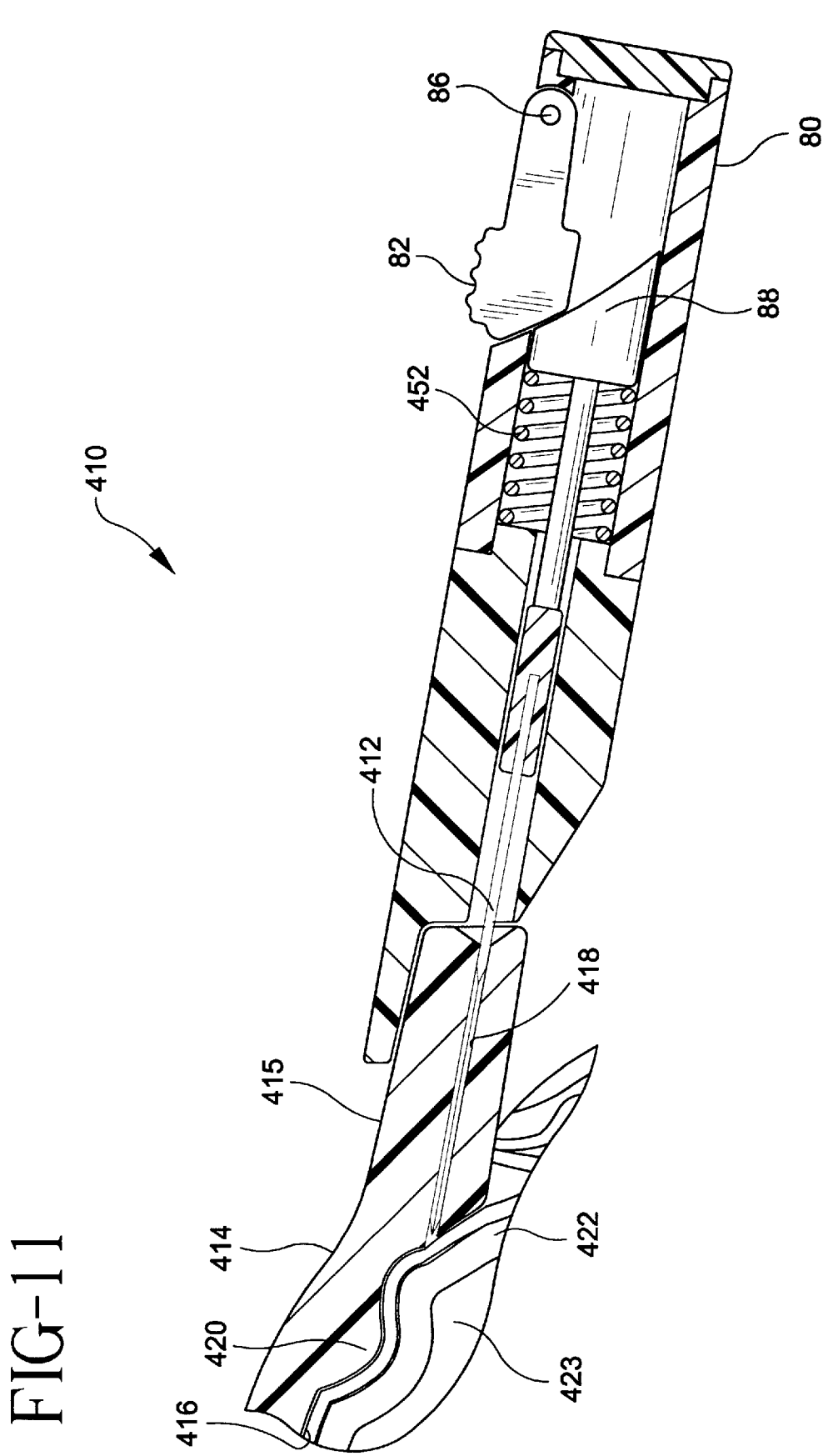
FIG. 11 is analogous to the view of FIG. 7 with a further blade movement system.

Referring to FIG. 11, projecting portion 415 from frame 414 of device 410 is illustrated. Projecting portion 415 includes a mechanical cam/cam follower mechanism 80 for advancing and retracting blade 412. When a practitioner applies sufficient finger pressure to cam 82, to overcome a bias spring 452, cam 82 pivots at pivot point 86 and cam follower 88 is urged distally to advance blade 412 a sufficient distance through aperture 418 to project beyond inner surface 416 of frame 414 to form the desired incision through surface 422 into the anterior chamber of patient eye 423. As the pressure is released from cam 82, bias spring 452 returns blade 412 to the original position where it no longer projects beyond inner surface 416.

Figure 12:
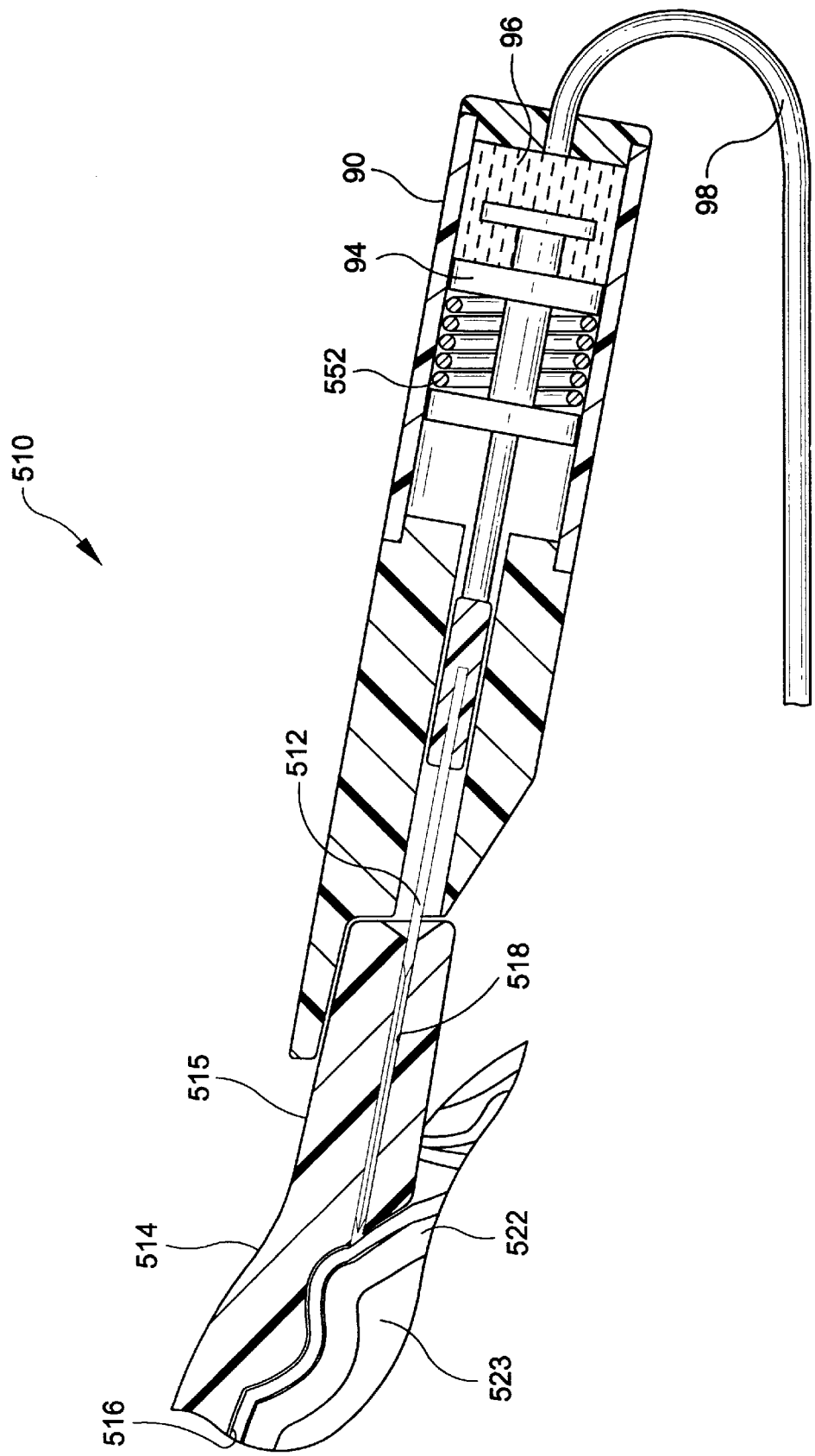
FIG. 12 is analogous to the view of FIG. 7 with an additional blade movement system.

Referring to FIG. 12, projecting portion 515 from frame 514 of device 510 is illustrated. Projecting portion 515 includes a hydraulic actuated mechanism 90 such as advancing a piston 94 against a bias spring 552 to urge blade 512 through aperture 518 to project beyond inner surface 516 and form the desired incision through patient eye surface 522 into the anterior chamber of the patient's eye. Other hydraulically actuation mechanisms such as an elastomeric diaphragm may be envisioned and are considered within the scope of this disclosure. The hydraulic pressure sufficient to overcome bias spring 552 is supplied from a source 98 having a valve. When the hydraulic pressure is released, bias spring 552 returns blade 512 to the original position within aperture 518.

The corneal incision device of the invention combines a placement and location device with the sharp surgical blade and the activation mechanism. This combination allows the practitioner to selectively place the location device on the patient's eye in the desired position, and once the desired placement is achieved, activate the surgical blade to make the complex incision without having to pick up another instrument. Thus, the correct placement of the device by the practitioner substantially ensures that the desired complex incision is formed and the rest of the procedure can then proceed.

What is claimed is:

1. A corneal incision device comprising:
a surgical blade;
a frame having an inner surface with a configuration that is generally in the shape of a ring-like segment of a hollow sphere where the frame defines an aperture therein to allow said surgical blade to be inserted through the frame beyond the inner surface, said aperture having a longitudinal axis and being sized and shaped to allow movement of said surgical blade only in said axis; means for holding in, advancing and withdrawing said surgical blade through said aperture, said means being disposed on said frame and including means for enabling the practitioner to selectively advance and withdraw said surgical blade a sufficient distance to penetrate the surface of the patient's eye to form an incision in the eye; means for releasable fixation of said device to the patient's eye disposed on the inner surface of the frame; and
a grip affixed to the frame to facilitate the practitioner's manipulation of said device.

2. The corneal incision device of claim 1 wherein said inner surface of said frame further includes a protuberance adjacent to said aperture disposed to distort a surface of a patient's eye when said device is selectively positioned on the eye by a practitioner.

3. The corneal incision device of claim 2 wherein said aperture has a proximal opening and a distal opening on said inner surface of said frame, said distal opening being substantially coterminous with said protuberance so that when said device is selectively positioned on the patient's eye and said blade is advanced through said distal opening an incision is made in the surface of the eye in a region of the eye surface under a strain caused by said protuberance.

4. The corneal incision device of claim 3 wherein said protuberance has a multi-plane topography.

5. The corneal incision device of claim 4 wherein said protuberance defines a substantially "S" shaped cross-section.

6. The corneal incision device of claim 1 wherein said longitudinal axis of said aperture forms an angle with said inner surface of said frame between about twelve degrees and about twenty degrees.

7. The corneal incision device of claim 6 wherein said longitudinal axis of said aperture forms an angle with said inner surface of said frame of about seventeen and one half degrees.

8. The corneal incision device of claim 1 wherein said surgical blade has a distal point having a beveled spear shaped sharp tip with sides that are dull as compared to said tip.

9. The corneal incision device of claim 1 further including activation means for activating said advancing means selected from the group consisting of an electrical contact, a valve and a mechanical release.

10. The corneal incision device of claim 1 wherein said advancing and withdrawing means are selected from the group consisting of a manually activated cantilever arm, a mechanical release including a bias spring, an electrical solenoid, a hydraulically actuated mechanism, a pneumatically actuated mechanism, a vacuum actuated mechanism, a cam and cam follower, a cable release against a mechanical biasing spring and combinations thereof.

11. The corneal incision device of claim 1 wherein said means for releasable fixation of said device to the eye of a patient are selected from the group consisting of lateral ridges on said inner surface of said frame, a plurality of bumps on said inner surface of said frame, a plurality of inward points on said inner surface of said frame, and at least one opening into said inner surface of said frame, so that when a selective application of a vacuum source to said device is applied and said device is selectively placed on the eye of a patient by the practitioner, ambient air pressure retains said device in a selected position as long as the vacuum source is applied and combinations thereof.

12. A corneal incision device comprising:
   a surgical blade;
   a frame having an inner surface with a configuration that is generally in the shape of a ring-like segment of a hollow sphere, where the frame defines an aperture therein to allow said surgical blade to be inserted through the frame beyond the inner surface, said aperture having a longitudinal axis and being sized and shaped to allow movement of said surgical blade in only said axis;
   a protuberance affixed to the inner surface of the frame adjacent to said aperture disposed to distort a surface of a patient's eye when said device is selectively positioned on the eye by a practitioner;
   a blade holder for holding said surgical blade for said movement of said surgical blade, said blade holder including a cantilever being biased to move said blade away from the surface of the patient's, eye said cantilever being disposed so that the practitioner can manually apply a force sufficient to overcome said bias to cause said cantilever to move said blade through said aperture and project into the surface of the patient's eye thereby making an incision in the surface of the eye, and withdraw said blade into said blade holder when the practitioner manually allows said bias to overcome the manually applied force;
   means for releasable fixation of said device to the patient's eye disposed on the inner surface of the frame; and
   a handle affixed to the frame to facilitate the practitioner's manipulation of said device.

13. The device of claim 12 wherein said blade holder including said cantilever further includes a manually releasable latch having a first position wherein said cantilever is substantially prevented from movement with respect to said frame and a second position wherein said cantilever is movable with respect to said frame by application of sufficient manual force to overcome said bias.

14. The device of claim 13 wherein said manually releasable latch further includes means for limiting a range of movement of said cantilever with respect to said frame when said latch is in said second position.

15. The device of claim 14 wherein said means for limiting said range of movement of said cantilever includes a boss disposed in an elongate slot, said slot defining said range of said movement.

* * * * *